United States Patent [19]

Kurono et al.

[11] Patent Number: 5,474,913
[45] Date of Patent: Dec. 12, 1995

[54] PROCESS FOR THE PREPARATION OF MOTILIN-LIKE POLYPEPTIDE AND EXPRESSION THEREOF

[75] Inventors: Masayasu Kurono; Takahiko Mitani; Haruo Takahashi; Kenichi Tanaka; Katsuya Fujimura; Kiichi Sawai, all of Aichi, Japan

[73] Assignee: Sanwa Kagaku Kenkyusho Co., Ltd., Aichi, Japan

[21] Appl. No.: 9,349

[22] Filed: Jan. 26, 1993

Related U.S. Application Data

[63] Continuation of Ser. No. 390,149, Aug. 7, 1989, abandoned.

[30] Foreign Application Priority Data

Aug. 24, 1988 [JP] Japan .................................. 63-208006

[51] Int. Cl.$^6$ ............................ C12P 21/02; C12P 15/00; C07H 21/04
[52] U.S. Cl. ...................... 435/69.4; 435/69.1; 435/69.8; 435/320.1; 536/23.51
[58] Field of Search ................................ 536/23.51, 25.3; 435/69.1, 69.4, 69.8, 172.1, 172.2, 172.3, 252.3, 320.1, 91.2; 935/6, 9, 22, 23, 52; 530/333

[56] References Cited

FOREIGN PATENT DOCUMENTS 63-71195   3/1988   Japan .

OTHER PUBLICATIONS

Seino et al., EMBASE Abstract No. 87218149, FEBS. Lett. (Netherlands), 1987.
Honda et al. Chem Ab. No. 109(15): 123801p Eur. Pat Appl. EP 259891 (Mar. 1988).
Strunz et al. Scand J. Gastroenterology, vol. 11, 119–203 (1976).
Morrow "Reconbinant DNA Techniques" in: Wu, *Reconbinant DNA, Methods in Enzymology*, vol. 68, (New York, Academic Press) pp. 3–24 (1979).
Alberts et al, *Molecular Biology of The Cell*, 2nd edition pp. 54–55, Garland publishing, N.Y., N.Y.
"Gastroenterology", J. C. Brown et al, vol. 62, pp. 401–404 (1972).
"Can. J. Biochem.,", J. C. Brown et al, vol. 52, pp. 7–8 (1974).
"Gastroenterology", N. D. Christofides et al, vol. 80, pp. 456–460 (1981).
"Scand. J. Gastroenterology", U. Strunz et al, vol. 11, pp. 119–203 (1976).

*Primary Examiner*—W. Gary Jones
*Assistant Examiner*—Lisa Arthur
*Attorney, Agent, or Firm*—Nikaido, Marmelstein, Murray & Oram

[57] ABSTRACT

Process for the preparation of motilin-like polypeptide, a recombinant DNA therefor, and a plasmid, in which the recombinant DNA is inserted.

5 Claims, 2 Drawing Sheets

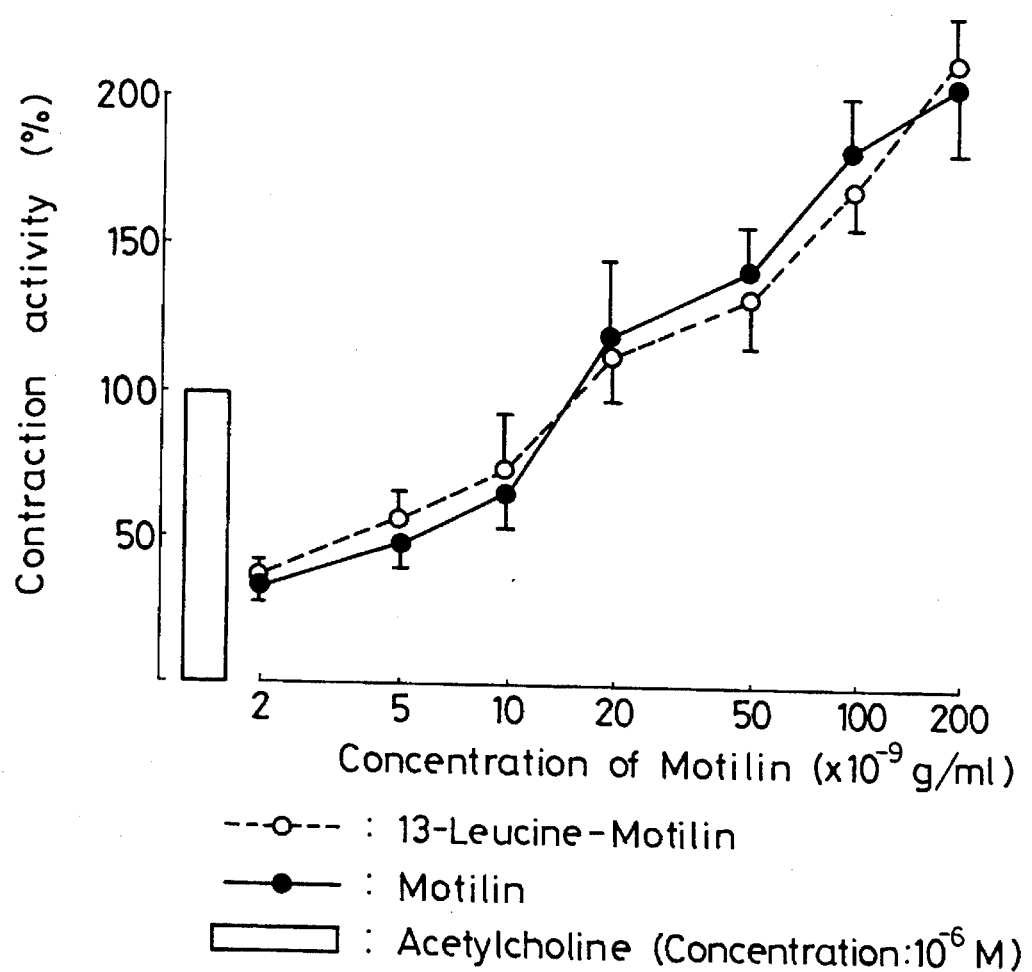

PROCESS FOR THE PREPARATION OF MOTILIN-LIKE POLYPEPTIDE AND EXPRESSION THEREOF

This application is a continuation of application Ser. No. 390,149, filed Aug. 7, 1989, now abandoned.

BACKGROUND OF THE INVENTION

1. Field of the Invention

The present invention relates to a process for the preparation of motilin-like polypeptide, a recombinant DNA therefor, and a plasmid, in which the recombinant DNA is inserted.

The polypeptide can be used as a pharmaceutical agent and more particulaly, for curing gastroenteropathies.

2. Related Arts

Motilin is one of peptide hormones, first isolated from mucous membrane of porcine upper small intestine, and its amino acid sequence determined by Brown J. C. et al ["Gastroenterology" Vol. 62, pages 401–404 (1972) and "Can. J. Biochem." Vol. 52, pages 7–10 (1974)]. The porcine motilin consists of 22 amino acids and has a molecular weight of about 2700.

The present inventors have succeeded in isolating cloned cDNA which encodes human motilin precursor, the nucleotide sequence including therein a part designating the amino acid sequence same with that for the porcine motilin, so that it has been made apparent that the human motilin has the same amino acid sequence same as the porcine motilin [Jap. Pat. No. Sho 63-276489(A) which corresponds to U.S. Pat. No. 4,985,356 and European Pat. Appln. No. 88107108.8].

As physiological actions of the motilin, a hypermotility action of digestive tract and contracting action of gastroduodinal and colonic smooth muscle therein have been well known. As the hypermotility action, it has been reported that the rate of gastric emptying is shortened ["Gastroenterology" Vol. 80, pages 456–460 (1981)] and as the contracting action of smooth muscle in the digestive tract, it has been known that the motilin shows a strong contracting action to rabbit and human gastrointesinal tract, independent from a neurosystem. Moreover, no report has been issued on any specific side-effect. Therefore, it has been considered that the motilin is useful for curing gastroenteropathies during the period of post-operation and for diagnosis thereof. In connection with this, please note that prostaglandin has widely been employed for curing gastroenteropathies, which drug may show a relatively strong side-effect.

It has been also reported that chemically synthesized motilin analogues—the methionine in position of 13 being substituted with either leucine or norleucine—show biological activities similar to pure native porcine motilin ["Scand. J. Gastroenterology" Vol. 11, pages 119–203 (1976) and others] and thus it has been considered that the methionine at 13-position has almost no influence on activity of the motilin.

Motilin according to widely accepted technical art has been obtained through extraction from porcine organ tissue and thus it was quite difficult to obtain motilin in a large amount by such methods. Since motilin is polypeptide consisting of 22 amino acids, a large scale production is difficult, even if chemical synthesis shall be applied. Namely, the motilin has not actually been employed for clinical use, due to its poor productivity, despite an effectiveness as an agent for curing gastroenteropathies has been expected.

Therefore, various studies have been made for preparing polypeptides having motilin-like biological activity, with a reasonable cost, by utilizing the so-called "Bio-technology" [Jap. Pat. Nos. 63-71195(A) and 1-102096(A)].

SUMMARY OF THE INVENTION

A basic object of the present invention is to provide a process for the preparation of motilin-like polypeptide, which is easier than any process developed prior to this invention.

An additional and important object of the invention is to provide a process for the preparation of motilin-like polypeptide, with a quite high efficiency.

Another object of the invention is to provide a novel recombinant DNA to be used for carrying out the process.

Still other object of the invention is to provide an expressing plasmid, whrein the recombinant DNA is inserted.

According to the invention, the basic object is attained by a process for the preparation of a motilin-like polypeptide of the formula (1)

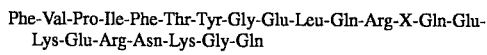

wherein X is an amino acid residue other than Met and Asp, which comprises a step for synthesizing each of a single-strand DNA having at least 6 amino acid residues having uncharged polar side chains and having methionine at terminal position thereof, its complementary single-strand DNA, a single-strand DNA encoding the amino acid sequence of said formula (1), and its complementary single-strand DNA, preparing a double-strand DNA with use of the resulting 4 single-strand DNA fragments and with the DNA fragment having the amino acid residues having uncharged polar side chains and its complementary DNA fragement, as a leader sequence, adding a specific restriction enzyme recognition site to each terminal site of the resulting double-strand DNA fragment, cleaving a plasmid having another protein hereditary information, with said restriction enzymes, ligating said double-strand DNA fragment to each cleaving site of the cleaved plasmid to re-construct as a plasmid having a recombinant DNA therein, transforming a microorganism with use of the re-constructed plasmid, cultivating the resulting transformant to produce as a part of fused protein the polypeptide encoding the amino acid sequence shown by said formula (1), breaking the microorganism and treating the fused protein with cyanogen bromide and endopeptidase to isolate the polypeptide of formula (1), and purifying the polypeptide through a fractionation.

The reason why the symbol X at 13-position amino acid residue is stated as the amino acid residue other than Met and Asp lies in that if X is Met, the desired polypeptide having a motilin-like activity cannot be obtained, since a cleavage will also occur at Met in 13-position, when the fused protein is treated with cyanogen bromide, and that X is Asp, the desired polypeptide can also not be obtained, since a cleavage will also occur at Asp in 13-position, through the treatment with the endopeptidase, which is required to remove excess amino acid residues, on the ground that the single-strand DNA corresponding to the polypeptide shown by formula (1) is separately synthesized, in order to make its synthesis convenient and there is a codon (GAC) encoding Asp after the amino acid sequence—Lys-Gly-Glu at C-terminal site. Each of the polypeptides to be obtained by the process according to the invention has a motilin-like biological activity, although the level of activity is different depending on the kind of amino acid residue represented by the symbol X. As the amino acid residue of X in 13-position, leucine (Leu), valine (Val) or the like is preferable. The polypeptides, wherein the amino acid residue in 13-position is glycine (Gly) or proline (Pro), are not preferable, since those show relatively low activity, as estimated from its stereo-structure. It has been found that asparagine (Asn), glutamine (Gln), threonine (Thr) and serine (Ser) are suitable as the amino acids having uncharged polar side chains, since the polypeptides with such an amino acid residue increase an expression efficiency. The ground of that the terminal amino acid residue in the leader polypeptide is methionine (Met) lies in that the leader sequence part can easily be removed out by the treatment with cyanogen bromide. According to the process of the invention, the single-strand DNA shown by formula (1) can be separately synthesized to make its synthesis easy.

The synthesized double-strand DNA encoding motilin-like gene substituted at 13-position can be inserted into a vector such as a plasmid with a conventional technique, for instance taking out the plasmid from *E. coli*, purifying the plasmid, treating the plasmid with a restriction enzyme to cut the same at a specific base position, and ligating with a DNA ligase the double-strand DNA to the cleavage site of the cut plasmid to re-construct a plasmid with the recombinant DNA. According to the process of the invention, further, a plasmid, wherein two or more 13-substituted motilin-like genes are inserted in tandem arrangement, can be prepared by treating a plasmid, in which the 13-substituted motilin-like gene is inserted, with two restriction enzymes to recover a fragment by cutting the plasmid at a portion upstream of the 13-substituted motilin-like gene and at another portion in the plasmid, treating another and same kind of plasmid having the recombinant DNA with the restriction enzyme same with that used for cutting the first plasmid at its inner portion and with another restriction enzyme which makes common the downstream site of the 13-substituted motilin gene part to the cleavage site of said upstream site, ligating with a DNA ligase said recovered fragment to the cleavage site in tandem arrangement to re-construct into a plasmid, and if necessary, repeating the procedures. In this case, it is preferable to connect between the 13-substituted motilin genes, with peptides, for instance those consisting of Asp-Gly-Ile-Phe-Met, since a cleavage will occur at Met-position, when cyanogen bromide acts in the leader polypeptide having at least 6 amino acid residues having uncharged polar side chains is connected with methionine of its C-teminal site, and further connected after its methionine with 13-substituted motilin, wherein the amino acid residue in 13-position is that other than methionine and aspartic acid. In this case, it is preferable that the polypeptide corresponding to the 13-substituted motilin is connected in plural and in tandem arrangement, and that each of the polypeptide encoding the 13-substituted motilin gene is connected with the peptides encoding the amino acid sequence of Asp-Gly-Ile-Phe-Met.

While, the expression plasmid according to the invention is characterized in that said recombinant DNA is inserted therein.

BRIEF DESCRIPTION OF THE DRAWING

FIG. 3 is a graph showing intestinal canal contraction activities of 13-leucine-motilin (which will be referred to later as [Leu$^{13}$]-motilin) obtained by the process according to the invention and a pure motilin obtained according to a conventional process were measured in accordance with the Magnus method.

DETAILED DESCRIPTION OF THE PREFERRED EMBODIMENTS

Figure 1:
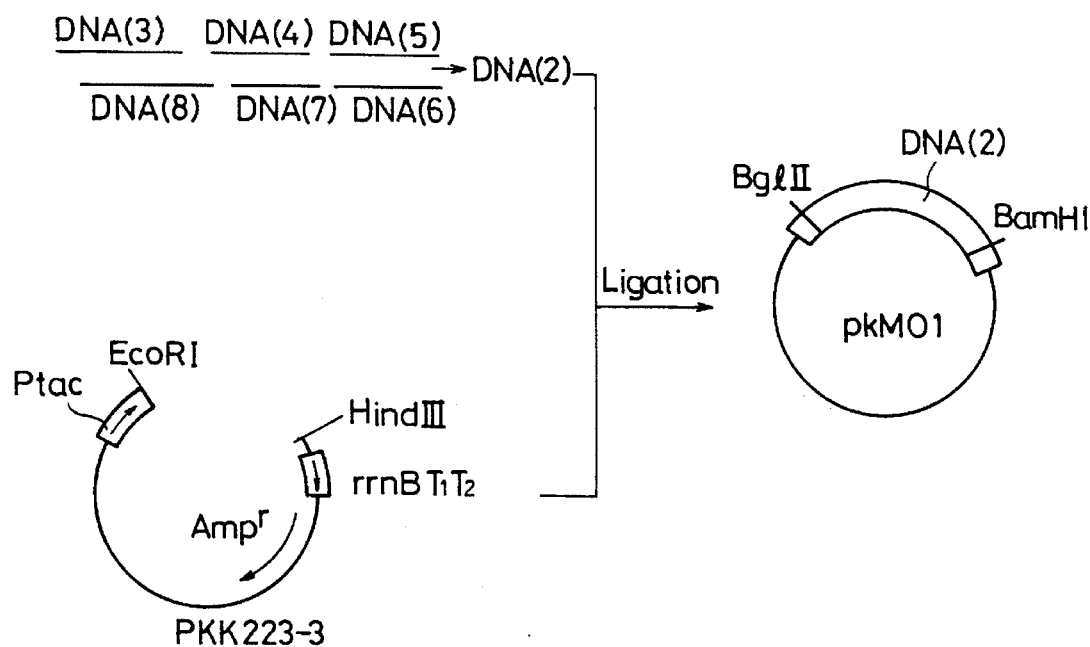
FIG. 1 is an illustration showing steps to prepare a plasmid having a recombinant DNA, wherein one motilin-like gene is inserted.

The invention will now be further explained with reference to Example and Test Example on pharmacological activity. In the below, the Example is concerned to a process for the preparation of the motilin-like polypeptide, wherein methionine of 13-position in motilin is exchanged into leucine, but please note other 13-substituted motilin-like polypeptides, wherein the amino acid residue in 13-position is other than methionine or aspartic acid, can be prepared by a method similar to that described in the Example.

EXAMPLE (1) Synthesis of DNA encoding the polypeptide having a motilin-like pharmacological activity It has been known that the human motilin has the following amino acid sequence.

```
         5              10          13    15              20
Phe—Val—Pro—Ile—Phe—Thr—Thy—Gly—Glu—Leu—Gln—Arg—Met—Gln—Glu—Lys—Glu—Arg—Asn—Lys—Gly—Gln
``` the step for separating the 13-substituted motilin-like polypeptide from the fused protein and another cleavage will occur at N-terminal of Asp, when an endopeptidase (Asp-N) acts to the resulting product, so that the 13-position exchanged motilin-like polypeptide can be obtained in the form having no excess peptide residue.

The motilin-like polypeptide can be prepared in a large amount by transforming a microorganism or eukaryotic cell with the plasmid, wherein one or more motilin-like genes is (are) inserted, and cultivating the microorganism or eukaryotic cell. As apparently seen from the above, the recombinant DNA according to the invention is characterized in that Further, it has been known that Met in 13-position has almost no influence on activity of the motilin.

Therefore, following double-strand DNA fragment shown in formula (2), which comprises a nucleotide sequence encoding an amino acid sequence for [Leu$^{13}$]-motilin, another nucleotide sequence encoding a leader peptide sequence with a number of amino acid residues having uncharged polar side chains (Met-Thr-Met-Ile-Thr-Asn-Ser-Asn-Gln-Asn-Gln-Asn-Gln-Asn-Gln-Asn-Gln-Asn-Gln-Ile-Phe-Met), said leader peptide encoding nucleotides being connected to the N-terminal site of [Leu$^{13}$]-motilin encoding nucleotides through methionine, and a still other nucleotide sequence encoding an amino acid sequence (Asp-Gly-Ile-Leu), which the last-mentioned nucleotide sequence is connected to the C-terminal site of [Leu$^{13}$]-motilin encoding nucleotides.

Formula (2)

```
5'- AATTCATGACCATGATTACGAACTCAAACCAAAACCAAAACCAAAACCAAACCA
3'-     GTACTGGTACTAATGCTTGAGTTTGGTTTTGGTTTTGGTTTTGGTTTTGG

AAACCAGATCTTCATGTTCGTTCCGATCTTCACCTACGGCGAACTGCAGCGTCT
TTTTGGTCTAGAAGTACAAGCAAGGCTAGAAGTGGATGCCGCTTGACGTCGCAG

GCAAGAAAAGAGCGCAACAAAGGCCAGGACGGGATCCTGTGATA
ACGTTCTTTTTCTCGCGTTGTTTCCGGTCCTGCCCTAGGACACTATTCGA
```

The double-strand DNA shown by formula (2) was synthesized as stated below.

In the first place, following 6 single-strand DNAs, each having following nucleotide sequence, were synthesized with use of a DNA synthesizer marketed as - - Gene Assembler - - from Pharmacia, Sweden. Among them, the DNAs (3) and (8), (4) and (7), as well as (5) and (6) are complementary strand with one another, except a terminal site thereof.

5'- AATTCATGACCATGATTACGAACTCAAACCAAAACCAAAACCAAAACCAAAACC AAAACCA   Formula (3)

5'- GATCTTCATGTTCGTTCCGATCTTCACCTACGGCGAACTGCAG   Formula (4)

5'- CGTCTGCAAGAAAAGAGCGCAACAAAGGCCAGGACGGGATCCTGTGATA   Formula (5)

5'- AGCTTATCACAGGATCCCGTCCTGGCCTTTGTTGGGCTCTTTTTCTTG   Formula (6)

5'- CAGACGCTGCAGTTCGCCGTAGGTGAAGATCGGAACGAACATGAA   Formula (7)

5'- GATCTGGTTTTGGTTTTGGTTTTGGTTTTGGTTTTGGTTTGAGTTCGTAATCAT GGTCATG   Formula (8)

Each of the single-strand DNAs shown by the formulae (3) to (8) was treated with a polynucleotide kinase to phosphorylate its 5'-terminal site, and then each of complementary DNA strand pairs of the formulae (3) and (8), (4) and (7) as well as (5) and (6) was annealed to prepare three double-strand DNAs. The resulting double-strand DNAs were ligated in tandem arrangement with use of DNA ligase to prepare the DNA fragment shown by said formula (2).

(2) Insertion of DNA fragment into an expression vector

Operation or procedure for inserting the DNA fragment synthesized in the manner described in Item (1) into an expression vector will be explained with reference to FIG. 1.

A commercially available vector to be used for an expression in E. coli (--pKK223-3--, plasmid marketed by Pharmacia, Sweden) was cut with use of restriction enzymes of Hind III and EcoRI. To ends of the resulting plasmid fragment, the synthesized DNA fragment was ligated with use of a DNA ligase to re-construct the plasmid fragment into an annular plasmid which was named pKM01. The re-constructed plasmid has been designed to initiate a protein synthesis at a position after 10 residues from SD-sequence downstream of Tac promoter and thus if the plasmid is inserted into E. coli to cultivate the same, it is possible to produce a protein with use of isopropylthio-β-D-galactopyranoside (IPTG) or the like.

Please note that the re-constructed vector has recognition sites to restriction enzymes of BglII and BamHI.

Figure 2:
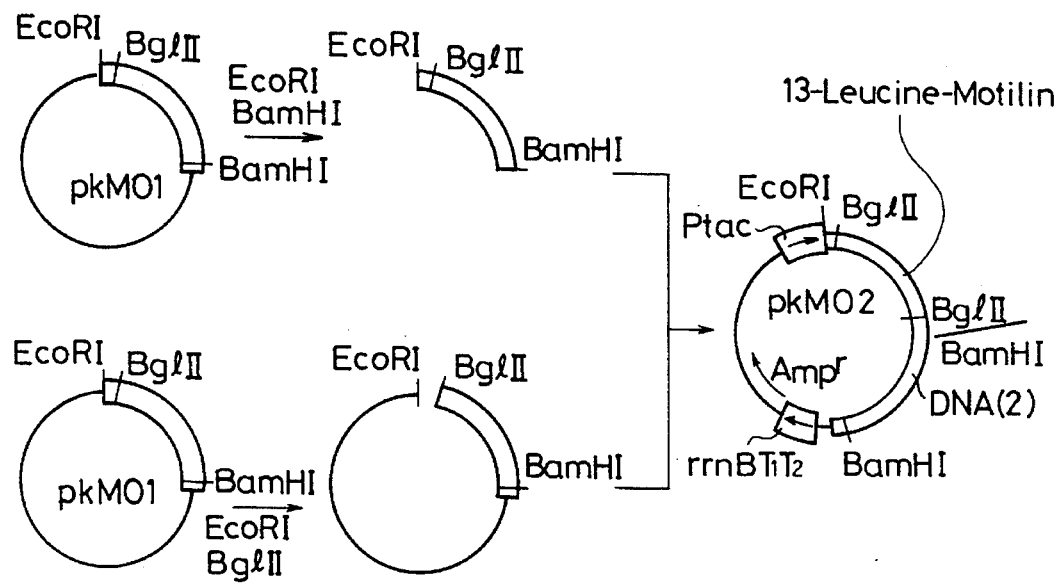
FIG. 2 is an illustration similar to that in FIG. 1, but two motilin-like genes are inserted in a plasmid, in tandem arrangement.

(3) Construction of expression plasmid having 2 or more genes of [Leu$^{13}$]-motilin This shall be explained with reference to FIG. 2.

In the first place, one of the plasmids (pKM01) obtained in the manner described in Item (2) was treated with restriction enzymes of EcoRI and BamHI to cut the plasmid at upstream of [Leu$^{13}$]-motilin gene part and at a part in the vector to recover a fragment. Then, another plasmid (pKM01) was treated with restriction enzymes of EcoRI and BglII to cut the plasmid, so that a cleavage site in the vector is common with that in the first plasmid and another cleavage site is at the downstream of [Leu$^{13}$]-motilin gene part in the second plasmid. To ends of the second plasmid fragment, said recovered fragment of the first plasmid was ligated with use of a DNA ligase to re-construct a plasmid which has two genes of [Leu$^{13}$]-motilin, and we named it pKM02. In this case, [Leu$^{13}$]-motilin genes are connected through a peptide encoding an amino acid sequence of Asp-Gly-Ile-Phe-Met.

Please note that the cleavage site due to the restriction enzyme of BamHI and the other cleavage site due to the restriction enzyme of BglII was ligated with use of the DNA ligase, so that the resulting ligated portion becomes a site which can not be recognized by each of the restriction enzymes. Therefore, a re-constructed plasmid having an optional number of [Leu$^{13}$]-motilin genes in tandem arrangement and a leader peptide sequence in upperstream thereof through methionine can be obtained by repeating said cleaving and ligating operations.

(4) Production of fused protein containing 13-leucine-motilin

A plasmid (pKM04) having an insert of tandem arranged four genes of [Leu$^{13}$]-motilin was employed. The plasmid was uptaken by E. coil (JM105) and the resulting transformant was subjected to an aeration culture under 30° C. in an ampicillin (50 μg/ml) containing culture medium (for instance, 0.5% casamino acid added M9 medium) and with use of a fermentor (D-type made by Able Co.). At the time when A$_{660}$ became 0.6–0.8, isopropylthio-β-D-galactopyranoside (IPTG) was added and its final concentration was made to 1.5mM.

Thereafter, the cultivation was continued over 16 hours and centrifuged (8000 rpm, 4° C., 5 minutes) to recover cells. A part of the cells were taken and analized by SDS polyacrylamide-gel electrophoresis (15%) to find that desired fused protein reaches about 30% of total protein. It was estimated that this good result was led by facts that the leader polypeptide sequence part in the synthesized DNA inserted in the plasmid accelerates with quite higher efficiency a formation of inclusion bodies, which are very stable to proteases.

(5) Isolation and purification of [Leu$^{13}$]-motilin

Paste cells (100 ml) obtained in the manner as described in Item (4) were suspended in 30 ml of 10 mM PBS-EDTA (pH 8.0) and the suspension was ultrasonically treated to break the cells. A residue of the cells was pelletized by a centrifugal treatment 18000 rpm, 30 minutes). The resulting pellet contains therein a fused protein of the leader peptide and a tetramer of [Leu$^{13}$]-motilin.

Therefore, the pellet (protein amount: about 100 mg) was dissolved in 30 ml of 70% formic acid. To the solution, 30 mg of cyanogen bromide were added and reacted over one night under the temperature condition lower than 37° C. Thereafter, distilled water (200 ml) was added and freeze-dried to remove the formic acid and cyanogen bromide. The resulting dried powder was dissolved in 0.1% trifluoroacetate and insoluble material removed. The resulting solution was injected to HPLC under following conditions:

Column: Micropondasphere C-18 (3.9 mm×15 cm), (made by Waters Co.)

Flow ratio: 0.8 ml/min.

Eluate: Linear gradient of 5% to 70% acetonitrile in 0.1% trifluoroacetate (40 minutes)

Fractions in a main peak part on the HPLC were recovered and freeze-dried. A part of the dried powder (100 µg) was taken and dissolved in 50 mM phosphate buffer (pH 8.0, 100 µl). After added thereto 0.1 µg of endoprotease Asp-N, marketed by Behringer Manheim GmbH, West Germany, the solution was reacted over 16 hours under 37°. The reaction solution was injected to HPLC under the conditions as above to obtain desired [Leu$^{13}$]-motilin as fractions in a main peak part.

A nucleotide sequence of this [Leu$^{13}$]-motilin was checked with use of a peptide sequencer marketed by Bio-Systems Co. to find that its sequence is right.

It has been found through the operations as above that 400–500 mg of the desired motilin-like polypeptide can be obtained by cultivation of 1 liter of *E. coli*.

Test on Biological Activity (Measurement of intestinal canal contraction activity)

An intestinal canal contraction activity was measured in accordance with the Magnus method utilizing a rabbit duodenum, ["J. Pharm. Pharmac." Vol. 28, pages 650–651 (1976)], on [Leu$^{13}$]-motilin obtained in the Example, as a test sample and a pure motilin obtained with use of a conventional extraction method, as a control sample. Results are shown in FIG. 3.

As apparently seen from the Figure, it has been confirmed that [Leu$^{13}$]-motilin obtained by the process of the invention has the intestinal canal contraction activity in the level same with that of the pure motilin, when a contraction caused by the reference substance of acetylcholine ($10^{-6}$M) is set as 100%.

What is claimed is:

1. A process for the preparation of a polypeptide of formula (I) Phe-Val-Pro-Ile-Phe-Thr-Tyr-Gly-Glu-Leu-Gln-Arg-X-Gln-Glu-Lys-Glu-Arg-Asn-Lys-Gly-Gln wherein X is an amino acids residue other than Met or Asp and which method consists essentially of the following steps:

(a) synthesizing a single-stranded DNA fragment encoding a leader polypeptide of the formula (II) Met-Thr-Met-Ile-Thr-Asn-Ser-Asn-Gln-Asn-Gln-Asn-Gln-Asn-Gln-Asn-Gln-Ile-Phe-Met and synthesizing its complementary single-stranded fragment;

(b) annealing the single-stranded fragments encoding the leader polypeptide made in step (a) to form a first double stranded DNA;

(c) synthesizing a single-stranded DNA fragment encoding a polypeptide of said formula I but with sequence Asp-Gly-Ile-Leu at the C-terminus and synthesizing its complementary single-stranded DNA fragment;

(d) annealing the single stranded DNA fragments encoding the polypeptide of formula (I) made in step (c) to form a second double-stranded DNA;

(e) ligating said first and second double-stranded DNAs so that the first and second double-stranded DNAs are in tandem arrangement;

(f) adding a recognition site for a specific restriction enzyme to both ends of the double stranded DNA made in step (e);

(g) cleaving a plasmid with said restriction enzyme;

(h) ligating the double-stranded DNA made in step (f) with the cleaved plasmid from step (g) to construct a recombinant plasmid;

(i) transforming a prokaryotic organism with said recombinant plasmid;

(j) cultivating the transformed prokaryotic organism such that a polypeptide is produced comprising the leader polypeptide of formula (II) fused at the N-terminus of the polypeptide of formula (I) having the sequence Asp-Gly-Ile-Leu at its C-terminus;

(k) lysing the transformed prokaryotic organisms after the cultivation step and treating with cyanogen bromide and endopeptidase to separate the leader polypeptide from the polypeptide of formula (I);

(l) fractionating the resulting mixture to purify the polypeptide of formula (I).

2. The process of claim 1 further comprising the steps of:

(i) cleaving the recombinant plasmid made in step (h) to generate a DNA fragment encoding the polypeptide of formula (I) having the oligopeptide Asp-Gly-Ile-Phe-Met fused to the C-terminus;

(ii) cleaving the recombinant plasmid made in step (h) at a restriction site downstream located from the sequence encoding the C-terminus of the polypeptide of formula (I)

(iii) ligating the DNA fragment from step (i) with the cleaved recombinant plasmid from step (ii) to construct a second recombinant plasmid which encodes the leader peptide fused to two tandem copies of the polypeptide of formula (I) which copies are connected by the oligopeptide Asp-Gly-Ile-Phe-Met;

(iv) repeating steps (i)–(iii) to further construct a recombinant plasmid encoding the leader peptide fused to at least three copies of the polypeptide of formula (I) each copy being connected by the oligopeptide Asp-Gly-Ile-Phe-Met;

(v) introducing the plasmid made in step (iv) into the prokaryotic organism of step (i).

3. An isolated recombinant DNA encoding a motilin-like polypeptide having a leader polypeptide of formula (II) Met-Thr-Met-Ile-Thr-Asn-Ser-Asn-Gln-Asn-Gln-Asn-Gln-Asn-Gln-Asn-Gln-Asn-Gln-Ile-Phe-Met fused to the N-terminus of a polypeptide having the sequence of formula (I) Phe-Val-Pro-Ile-Phe-Thr-Tyr-Gly-Glu-Leu-Gln-Arg-X-Gln-Glu-Lys-Glu-Arg-Asn-Lys-Gly-Gln, wherein X is an amino acid other than Met or Asp, and wherein the polypeptide having the sequence of formula (I) has the oligopeptide Asp-Gly-Ile-Leu at the C-terminus.

4. An expression vector for preparing a motilin-like polypeptide containing a DNA fragment encoding a motilin-like polypeptide having a leader polypeptide of formula (II) Met-Thr-Met-Ile-Thr-Asn-Ser-Asn-Gln-Asn-Gln-Asn-Gln-Asn-Gln-Asn-Gln-Ile-Phe-Met fused to the N-terminus of a polypeptide having the sequence of formula (I) Phe-Val-Pro-Ile-Phe-Thr-Tyr-Gly-Glu-Leu-Gln-Arg-X-Gln-Glu-Lys-Glu-Arg-Asn-Lys-Gly-Gln, wherein X is an amino acid other than Met or Asp.

5. The expression vector of claim 4 further containing at least two additional tandem copies said DNA fragment, wherein each copy is connected by an oligopeptide having the sequence Asp-Gly-Ile-Phe-Met.

* * * * *